US009168218B2

(12) United States Patent
Dimotakis et al.

(10) Patent No.: US 9,168,218 B2
(45) Date of Patent: Oct. 27, 2015

(54) USE OF PHOTOLUMINESCENT POLYMERS IN COSMETIC PRODUCTS

(75) Inventors: Emmanuel Dimotakis, Oradell, NJ (US); Hy Si Bui, Piscataway, NJ (US); Jean-Thierry Simonnet, Mamaroneck, NY (US); Mohamed Kanji, Edison, NJ (US)

(73) Assignee: L'OREAL S.A. (FR)

( * ) Notice: Subject to any disclaimer, the term of this patent is extended or adjusted under 35 U.S.C. 154(b) by 0 days.

(21) Appl. No.: 13/357,923

(22) Filed: Jan. 25, 2012

(65) Prior Publication Data

US 2012/0189562 A1 Jul. 26, 2012

Related U.S. Application Data

(60) Provisional application No. 61/436,016, filed on Jan. 25, 2011.

(51) Int. Cl.

| *A61K 8/85* | (2006.01) |
|---|---|
| *A61Q 17/04* | (2006.01) |
| *A61Q 1/02* | (2006.01) |
| *A61Q 5/06* | (2006.01) |
| *A61Q 1/10* | (2006.01) |
| *A61Q 19/02* | (2006.01) |
| *A61Q 1/04* | (2006.01) |
| *A61Q 5/02* | (2006.01) |
| *A61Q 5/12* | (2006.01) |

(52) U.S. Cl.
CPC ... *A61K 8/85* (2013.01); *A61Q 1/02* (2013.01); *A61Q 5/06* (2013.01); *A61Q 17/04* (2013.01); *A61K 2800/434* (2013.01); *A61Q 1/04* (2013.01); *A61Q 1/10* (2013.01); *A61Q 5/02* (2013.01); *A61Q 5/12* (2013.01); *A61Q 19/02* (2013.01)

(58) Field of Classification Search
CPC .......................... A61K 2800/434; A61K 8/85
See application file for complete search history.

(56) References Cited

U.S. PATENT DOCUMENTS

| 4,537,782 | A | * | 8/1985 | Millet et al. ................... 514/774 |
|---|---|---|---|---|
| 5,292,512 | A | * | 3/1994 | Schaefer et al. ............... 424/401 |
| 5,364,633 | A | | 11/1994 | Hill et al. |
| 5,411,744 | A | | 5/1995 | Hill et al. |
| 6,592,882 | B2 | * | 7/2003 | George et al. ................... 424/401 |
| 8,530,611 | B2 | * | 9/2013 | Yang et al. ..................... 528/289 |
| 2004/0241126 | A1 | * | 12/2004 | Sakuta ........................ 424/70.12 |
| 2006/0083694 | A1 | * | 4/2006 | Kodas et al. .................... 424/46 |
| 2006/0229222 | A1 | | 10/2006 | Muller et al. |
| 2010/0015074 | A1 | | 1/2010 | Blin |
| 2010/0190740 | A1 | | 7/2010 | L'Alloret et al. |
| 2010/0278770 | A1 | | 11/2010 | Arditty et al. |

FOREIGN PATENT DOCUMENTS

| EP | 0107199 | A2 | | 5/1984 |
|---|---|---|---|---|
| GB | 2131820 | | | 6/1984 |
| JP | 2010043028 | A | * | 2/2010 |
| WO | 9400508 | A1 | | 1/1994 |
| WO | WO 2007143209 | A2 | * | 12/2007 |
| WO | 2009155450 | A2 | | 12/2009 |
| WO | WO 2009155450 | A2 | * | 12/2009 |

OTHER PUBLICATIONS

Mary Kay Makeup Web page, 2013, Mary Kay Cosmetics.*
Cerny et al (Food Chemistry, 2013, vol. 141, pp. 1078-1086).*
Nash et al (Organic Letter, 2013, vol. 15, pp. 4770-4773).*
Bishop et al (Langmuir, 2012, vol. 28, pp. 1322-1329).*
Rizzacasa et al (Organic and Biomolecular Chemistry, 2014, vol. 12, p. 1367-1382).*
PhytoClinic (Creams and Lotions, http://www.phytoclinic.com/phyto-pharmacy/creams-lotions.html, 2014).*
Yang et al. (Proclamation of the National Academy of Sciences, Jun. 2009, vol. 106, pp. 10086-10091).*
Dey et al., "Development of biodegradable crosslinked urethane?doped polyester elastomers", Biomaterials 2008, 29:4637?4649.
Gyawali et al., "Citric acid?derived in situ crosslinkable biodegradable polymers for cell delivery", Biomaterials 2010 DOI:10.1016/j.biomaterials, 2010.08.022.
Gyawali et al., "Citric acid?derived photocrosslinked biodegradable elastomers", Journal of Biomaterials Science: Polymer Edition 2010, 21: 1761?1782.
Seurer et al., "Ethylene-Propylene-Silsesquioxane Thermoplastic Elastomers", Macromolecular Chemistry and Physics (2008), 209.
Tran et al., "Recent developments on citric acid derived biodegradable elastomers", Recent Patents on Biomedical Engineering 2009, 2, 216-227.
Tran et al., "Synthesis and characterization of a biodegradable elastomer featuring a dual crosslinking mechanism", Soft Matter, 2010, 6: 2449?2461.
Yang et al., "Development of aliphatic biodegradable photoluminescent polymers", Proceedings of the National Academy of Sciences of the United States of America 2009 106:10086?10091.
Yang et al., "Novel citric acid?based biodegradable elastomers for tissue engineering", Advanced Materials, 2004,16(6):511?516.
Yang et al., "Synthesis and evaluation of poly(diol citrates) biodegradable elastomer", Biomaterials 2006,27: 1889?1898.
Zhang et al., "Development of photocrosslinkable urethanedoped polyester elastomers for soft tissue engineering", International Journal of Biomaterials Research and Engineering, 1(1), 18-31, Jan.-Mar. 2011, 2010 Submitted.

* cited by examiner

*Primary Examiner* — Brian-Yong Kwon
*Assistant Examiner* — Mark V Stevens
(74) *Attorney, Agent, or Firm* — Lerner, David, Littenberg, Krumholz & Mentlik, LLP (57) ABSTRACT

Disclosed are cosmetic compositions and methods for making up keratinous tissue using the compositions, as well as methods of making the compositions. The compositions contain a photoluminescent polymer (PLP) which is an oligomeric polyester synthesized from a multifunctional monomer and a diol, and which has grafted thereon an amino acid or an amino acid derivative. The compositions achieve a colorizing and/or UV-protectant effect when applied to keratinous tissue.

37 Claims, 1 Drawing Sheet

USE OF PHOTOLUMINESCENT POLYMERS IN COSMETIC PRODUCTS

CROSS-REFERENCE TO RELATED APPLICATIONS

The present application claims the benefit of the filing date of U.S. Provisional Patent Application No. 61/436,016 filed Jan. 25, 2011, the disclosure of which is hereby incorporated herein by reference.

BACKGROUND OF THE INVENTION

Over-exposure to solar radiation is known to cause sunburn, skin damage and an increased risk of developing skin cancer, as well as photo-augmented skin aging. To safeguard against these risks, sun protection materials are applied to the skin, particularly for purposes of engaging in outdoor activities. In addition to their capacity to screen sunlight, the photoprotective compounds, which are typically organic molecules that protect against UV-A and/or UV-B rays, must also have good cosmetic properties, effective solubility in customary solvents, including both aqueous media and oils and fats, exhibit good resistance to water and perspiration (persistence) and satisfactory photostability. However, a large number of soluble organic filters can cause compatibility problems with the usual ingredients of cosmetic compositions mainly because of interactions with other filters or active organic agents such as antioxidants or vitamins that may be present, the result being that the photostability effect is not entirely satisfactory. Solving this latter problem is the subject of numerous patents, revealing how this problem is recurrent.

In addition to protecting the skin against exposure to UV light, the cosmetics industry also engages in continuous efforts to develop new formulas to lighten the skin. The substances most commonly used as bleaching agents include hydroquinone and its derivatives, kojic acid and its derivatives, azelaic acid, arbutin and its derivatives, alone or in combination with other active agents. These bleaching agents are not without drawbacks. For example, they frequently need to be used for a long time and in large amounts in order to obtain a bleaching effect on the skin. No immediate effect is observed on applying compositions comprising them. In addition, when hydroquinone and its derivatives are used in an amount that is effective to produce a visible bleaching effect, hydroquinone is known for its cytotoxicity towards melanocytes. Moreover, kojic acid and its derivatives can have the drawback of being expensive and consequently of not being able to be practicably used in large amounts in products for commercial mass distribution.

Other approaches to skin lightening entail application of cosmetic compositions capable of unifying the complexion, and which may give an immediate white appearance. These compositions include powders dispersed in a binder, wherein the powders are generally white or coloured pigments depending on the desired effect and/or fillers of various shapes (lamellar or spherical) depending on the desired effect. The drawback of such compositions is that the fading-out of the skin defects is provided by the covering power of the compositions. Skin that has thus been made up loses its natural look owing to the lack of transparency of these compositions.

To overcome these drawbacks, the use of optical brighteners such as stilbene derivatives, coumarin derivatives, oxazole and benzoxazole derivatives and imidazole derivatives has been proposed. Optical brighteners are bleaching agents that have fluorescent properties, absorbing in the ultraviolet range (maximum absorption at a wavelength of less than 400 nm) and re-emitting the energy by fluorescence at a wavelength of between 380 nm and 830 nm. An energy emission of between 400 nm and 480 nm results in an emission in the blue region of the visible field, which contributes, when this emission takes place on the skin, towards visually bleaching it. The optical brighteners are generally dispersed directly in the cosmetic formulations under consideration, which may, in certain cases, affect their physicochemical stability, and will do so proportionately more the greater their concentration in the compositions. Moreover, the introduction of these starting materials into compositions for topical use is limited by toxicological constraints. Since the lightening effect is directly linked to the amount of optical brightener used, it decreases when the concentration of optical brightener used is minimized.

Thus, there remains a need for cosmetic products for application to the skin that provide adequate protection against the hazards of over-exposure to U.V. radiation and to provide a skin lightening effect but which are safer to use.

BRIEF SUMMARY OF THE INVENTION

The present invention provides novel cosmetic compositions and methods of making up keratinous tissue in a way that provides not only a UV-protectant effect but a skin enlightening and/or colorizing effect as well. The present invention exploits the use of photoluminescent polymers that are polyesters having grafted thereon or incorporated into the backbone or skeleton thereof an amino acid or an amino acid derivative. The PLPs may be crosslinked or non-crosslinked.

A first aspect of the present invention is directed to a cosmetic composition, comprising a photoluminescent polymer (PLP) which is an polyester synthesized from (the polymerization product of) a multifunctional monomer containing two carboxylic acid groups and a functional moiety comprising a carboxylic acid group or a hydroxyl group, and a diol, and which has grafted thereon or incorporated into the polymer backbone, an amino acid or an amino acid derivative, a solvent and at least one cosmetically acceptable ingredient.

A second aspect of the present invention is directed to a method of making up keratinous tissue, comprising applying to keratinous tissue a cosmetic composition, comprising a photoluminescent polymer (PLP) which is an polyester synthesized from a multifunctional monomer containing two carboxylic acid groups and a functional moiety comprising a carboxylic acid group or a hydroxyl group, and a diol, and which has grafted thereon or incorporated into the polymer backbone, an amino acid or an amino acid derivative, a solvent and at least one cosmetically acceptable ingredient.

A third aspect of the present invention is directed to a method of preparing a cosmetic composition for making up keratinous tissue, comprising formulating a photoluminescent polymer (PLP) which is an polyester synthesized from a multifunctional monomer containing two carboxylic acid groups and a functional moiety comprising a carboxylic acid group or a hydroxyl group, and a diol, and which has grafted thereon or incorporated into the polymer backbone, an amino acid or an amino acid derivative, a solvent and at least one cosmetically acceptable ingredient.

Without intending to be bound by any particular theory of operation, Applicants believe that the UV protectant colorizing, and enlightening effects are achieved by the capability of the PLP to absorb light outside of the visible range (e.g., UV-A light) and emit light in the visible range with good quantum yield, and with substantially the same intensity in which the light is absorbed.

Aside from these beneficial properties that the PLPs impart to cosmetic compositions, which allow them to be used in the inventive compositions and methods as a sole or primary UV filter or colorant (e.g., without the presence of a colorant), the solubility of the PLPs in both aqueous and non-aqueous polar solvents gives them tremendous versatility in that they are amenable to being formulated into virtually any type of cosmetic composition for purposes of making up keratinous tissue. In addition, the film formed on the keratinous tissue by the PLP provides for a relatively long colorizing and/or UV protectant effect, as compared to traditional colorants and UV protectants which are more easily washed away. Even further, the PLPs exhibit controlled degradability.

Yet another advantage of the present invention lies in the non-toxic and environmentally friendly nature of the PLPs. Cosmetic compositions contain an appreciable amount of synthetic products, especially formulation additives, to give them specific properties such as satisfactory stability over time and/or with regard to significant variations in temperature, satisfactory behavior especially in terms of makeup qualities, and good applicability. However, in the cosmetics field where the turnover of products is extremely rapid, there is a constant need for novel formulation routes for obtaining a level of performance at least equal to that offered by the current products, or, in certain respects, even better. Moreover, the choice of raw materials used for the implementation of these novel formulation routes must be guided, as it has always been, by an ever-increasing concern to offer the maximum guarantee, both for the consumers for whom the cosmetic formulations that incorporate them are intended, and for preservation of the integrity of the environment. Both the PLPs themselves and their starting materials, as well as at least one other cosmetic ingredient that may be present in the inventive compositions, are made of biodegradable and replenishible ingredients.

DETAILED DESCRIPTION

Figure 1:
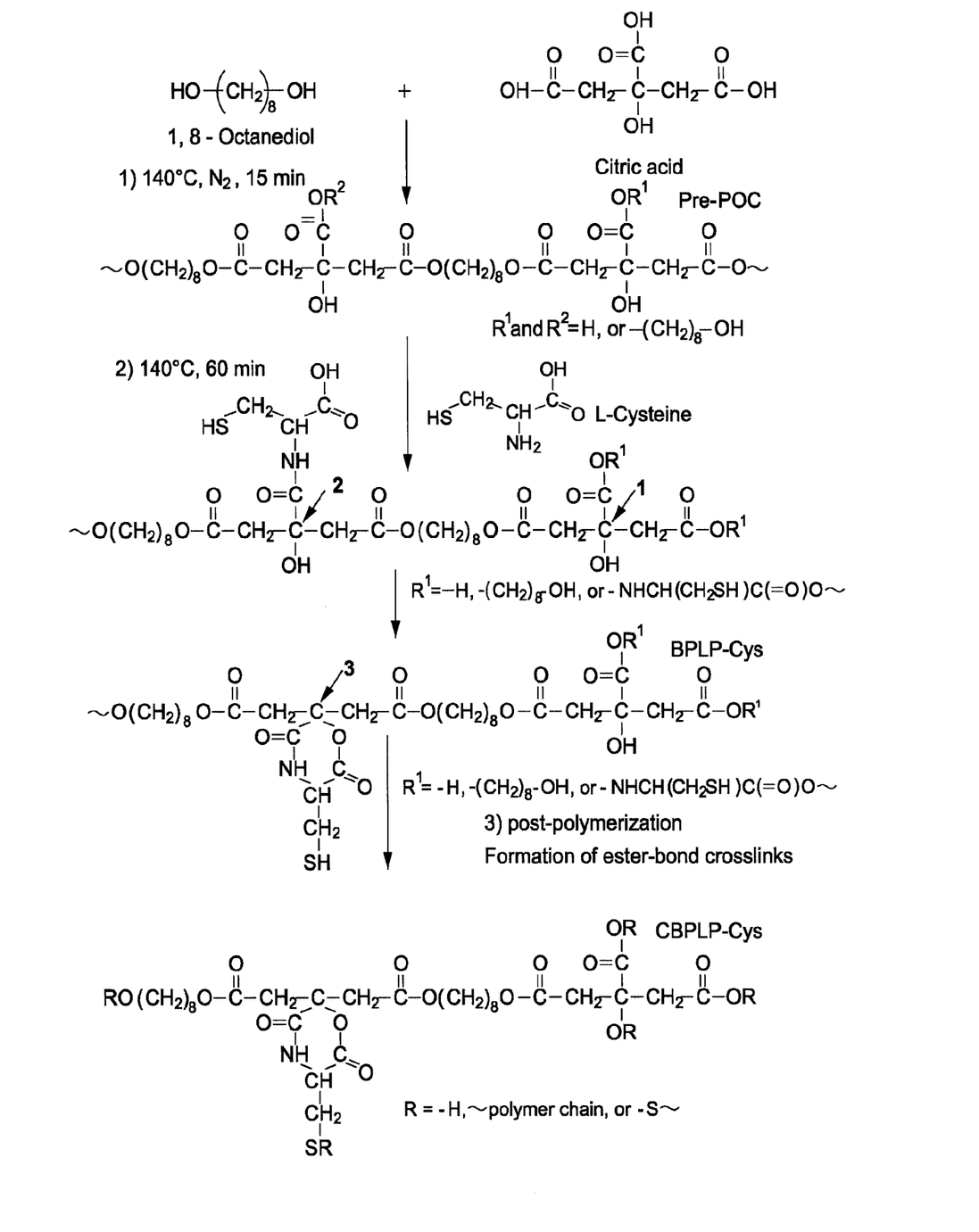
The FIGURE is a schematic view of a synthesis for a PLP of the present invention.

Other than in the operating examples, or where otherwise indicated, all numbers expressing quantities of ingredients and/or reaction conditions are to be understood as being modified in all instances by the term "about," meaning within 10% to 15% of the indicated number.

"Keratinous tissue", as used herein, includes but is not limited to, skin (including scalp), hair and nails.

"Substituted" as used herein, means comprising at least one substituent. Non-limiting examples of substituents include atoms, such as oxygen atoms and nitrogen atoms, as well as functional groups, such as hydroxyl groups, ether groups, alkoxy groups, acyloxyalky groups, oxyalkylene groups, polyoxyalkylene groups, carboxylic acid groups, amine groups, acylamino groups, amide groups, halogen-containing groups, ester groups, thiol groups, sulphonate groups, thiosulphate groups, siloxane groups, and polysiloxane groups. The substituent(s) may be further substituted.

"Volatile", as used herein, means having a boiling point of less than about 100° C. "Non-volatile", as used herein, means having a flash point of greater than about 100° C.

As used herein, the terms "at least one", "a", and "an" mean one or more and thus include individual components as well as mixtures/combinations.

"Long wear" compositions as used herein, refer to compositions where color remains the same or substantially the same as at the time of application, as viewed by the naked eye, after an extended period of time. Long wear properties may be evaluated by any method known in the art for evaluating such properties. For example, long wear may be evaluated by a test involving the application of a composition to human hair, skin or lips and evaluating the color of the composition after an extended period of time. For example, the color of a composition may be evaluated immediately following application to hair, skin or lips and these characteristics may then be re-evaluated and compared after a certain amount of time. Further, these characteristics may be evaluated with respect to other compositions, such as commercially available compositions.

"Hardness" as used herein, refers to the resistance of a composition to penetration. Hardness may be evaluated according to a method of penetrating a probe into the composition and in particular using a texture analyzer (for example TA-XT2i from Rheo) equipped with an ebonite cylinder of height 25 mm and diameter 8 mm. The hardness measurement is carried out at 20° C. at the center of 5 samples of the composition. The cylinder is introduced into each sample of composition at a pre-speed of 2 mm/s and then at a speed of 0.5 mm/s and finally at a post-speed of 2 mm/s, the total displacement being 1 mm. The recorded hardness value is that of the maximum peak observed.

The Photoluminescent Polymers (PLP)

The present invention utilizes aliphatic photoluminescent polymers (referred to herein as PLPs) and their associated crosslinked variants (referred to herein as CPLPs) for cosmetics applications. The PLPs of the present invention are biodegradable and may be referred to as oligomeric in that they have a molecular weight (MW) of at least about 2,000. They may be synthesized using as starting materials, biocompatible multifunctional monomers including citric acid, aliphatic diols, and amino acids, via known procedures such as a convenient and cost-effective polycondensation reaction, as described for example in WO 2009/155450 and in Yang, et al., Proc. Nat'l Acad. Sci. USA 106(25):10086-91 (2009). A schematic view of a synthesis for a PLP of the present invention is shown in The FIGURE. The PLPs exhibit a fluorescence which is believed to emanate from a 6-membered aliphatic ring formed by a carboxylic acid, an alpha carbon, and an amino group of an amino acid. The carboxylic acid, the alpha carbon and the amino groups bend backwards to join the polymer backbone via an esterification reaction.

As used herein, the term "multifunctional monomers" describes monomers including citric acid and its derivatives such as triethyl citrate that contain at least two carboxylic acid groups and a third functional moiety which is a carboxylic acid or a hydroxyl group. The multifunctional monomer such as citric acid can be partially replaced by unsaturated dicarboxyl monomers to make unsaturated PLPs. The unsaturated carboxylic monomers include, for example, vinyl-containing maleic acid, maleic anhydride, fumaric acid, fumaryl chloride, and acroylchloride which have at least one carbon-carbon double bond.

Representative diols include saturated aliphatic diols including saturated diols such as $C_3$-$C_{12}$ diols, macrodiols, hydrophilic diols, hydrophobic diols and combinations thereof, and unsaturated diols (e.g., C3-C12 diols) such as cis-2-butene-1,4-diol. Examples of specific diols include 1,8-octanediol, ethylene diol, propylene diol, poly(ethylene glycol), poly(propylene glycol), 1,3-propanediol, ethanediol, and cis-1,2-cyclohexanediol.

Representative amino acids include L-amino acids, D-amino acids, D,L-amino acids and their derivatives and combinations. Both naturally-occurring and non-naturally occurring amino acids may be used. The twenty (20) naturally occurring amino acids which are particularly useful to make the PLPs of the present invention include Alanine (Ala), Arginine (Arg), Asparagine (Asn), Aspartic acid (Asp), Cysteine (Cys), Glutamic acid (Glu), Glutamine (Gln), Glycine (Gly), Histidine (His), Isoleucine (Ile), Leucine (Leu), Lysine (Lys), Methionine (Met), Phenylalanine (Phe), Proline (Pro), Serine (Ser), Threonine (Thr), Tryptophan (Trp), Tyrosine (Tyr) and Valine (Val), and derivatives thereof capable of forming similar cyclic structures, representative examples of which include aryl (e.g., benzyl and phenyl) esters (e.g., S-benzyl-L-cysteine, S-phenyl-S-cysteine, tryptophan benzyl ester); alkyl (e.g., lower alkyl) esters (e.g., S-methyl-cysteine, L-histidine methyl ester, phenylalanine methyl ester, L-tyrosine methyl ester); and alkyl-substituted (e.g., lower alkyl-substituted) amino acids (e.g., 1-methyl-L-histidine, 1-methyl-D-tryptophan, 1-methyl-L-tryptophan. In some embodiments, the amino acids are selected from cysteine, histidine, phenylalanine, tryptophan and tyrosine. As used herein "lower alkyl" refers to C1-C6, preferably C1-C5, more preferably C1-C4, and most preferably C1-C3.

In some embodiments, the PLPs are made from citric acid, 1,8-octanediol and one of the twenty L-amino acids. The colorizing effect of the composition, at least to a certain extent, is influenced by the side chain pendant to the alpha carbon in the amino acid. As shown in Table 1, which contains data with respect to various properties of these PLPs, including range of excitation and emission wavelengths and quantum yield, the emission spectra and quantum yields differ from amino acid to amino acid.

TABLE 1

Range of excitation and emission wavelengths and quantum yields for BPLPs with twenty different amino acids.

| BPLP- | Exc (nm) | Emi (nm) | Quantum yield (%) |
|---|---|---|---|
| Ala | 250-413 | 295-524 | 5.3 |
| Arg | 250-503 | 297-594 | 0.9 |
| Asn | 280-490 | 299-623 | 11.0 |
| Asp | 275-415 | 301-493 | 11.4 |
| Cys | 240-420 | 312-561 | 62.3 |
| Glu | 255-415 | 296-647 | 0.3 |
| Gln | 280-500 | 296-647 | 13.9 |
| Gly | 265-510 | 295-678 | 10.9 |
| His | 310-540 | 330-650 | 1.9 |
| Ile | 250-403 | 291-499 | 1.2 |
| Leu | 275-415 | 311-525 | 1.0 |
| Lys | 265-535 | 291-646 | 9.4 |
| Met | 250-396 | 286-491 | 0.5 |
| Phe | 270-420 | 294-498 | 0.8 |
| Pro | 255-450 | 294-533 | 0.4 |
| Ser | 290-660 | 303-725 | 26.0 |
| Thr | 250-470 | 313-580 | 34.2 |
| Trp | 300-490 | 340-588 | 12.1 |
| Tyr | 240-440 | 311-561 | 3.1 |
| Val | 240-391 | 279-495 | 1.0 |

BPLP-amino acid solutions (1% w/w in 1,4-dioxane) were used for photoluminescence characterization.

As shown in Table 1, cysteine, serine and threonine exhibit relatively high good quantum yield.

The unsaturated PLPs can be further polymerized or crosslinked via radical polymerizations initiated by photoinitiators and/or redox initiators, or by thermal polymerization. The unsaturated PLPs can be further copolymerized or crosslinked with other vinyl-containing monomers such as acrylic monomers. Representative examples of vinyl-containing monomers include acrylates and methacrylates, e.g., diacrylates, triacrylates, dimethacrylates, and trimethacrylates, multifunctional allylic compounds, such as diallyl maleate and allyl methacrylate, as well as multifunctional monomers having a vinyl functionality such as allyl methacrylate (AMA), diallyl maleate (DAM), divinyl benzene (DVB), ethylene glycol dimethacrylate (EGDMA), N,N'-methylene-bis-acrylamide (NNMBA), tripropylene glycol diacrylate (TPGDA), triallyl cyanurate (TAC), triethylene glycol dimethacrylate (TEDMA, TEGMA), trimethylolpropane triacrylate (TMPTA), trimethylolpropane trimethacrylate (TMPTMA, TRIM), and trimethylolpropane diallyl ether (TMPDAE). Methods of synthesizing crosslinked urethane-doped PLP (CUPLP), water-soluble PLP (WPLP), and photo-crosslinkable PLP (PCPLP) are also disclosed in the forementioned publications.

In general, the amount of PLP ranges from about 0.001% to about 99% and in some embodiments from about 0.5% to about 80%, and in some embodiments from about 5% to about 60%, and in some other embodiments from about 5% to about 40%, and in yet other embodiments, from about 7% to about 20% by weight, based on the total weight of the composition.

Main Types of Cosmetic Compositions

Broadly, cosmetic compositions in which the PLPs may be formulated fall into three general categories, namely: anhydrous-based compositions; aqueous-based compositions wherein water is present as a major ingredient; and multiphasic compositions or emulsions, that include two or more phases that are aqueous and oil-based, wherein the discrete (e.g., continuous and discontinuous) phases are dispersible by the presence of an emulsifier or other cosmetic ingredient with emulsifying properties.

Anhydrous Compositions

In these types of compositions, aside from an amount of water present in a pre-made commercial cosmetic ingredient, there is typically no added water. For purposes of the present invention, added water may be present in amounts of no more than 10%, 5%, 2% or even 1%, based on the total weight of the composition. Representative examples of anhydrous cosmetic compositions include non-compressed and compressed powders (such as foundation, and sticks), pastes, water-proof mascara, lipstick and lipgloss, and hair care products.

In addition to the PLP and non-aqueous polar solvent, these compositions typically contain at least one additional cosmetic ingredient, including for example, structuring agents such as waxes and non-wax polymers, hydrophobic gelling agents, and powders/fillers.

Aqueous-Based Compositions

Representative examples of aqueous-based cosmetic compositions include washable mascara, lipstick, lipgloss, lip balm, lotions and gels, and hair care products (e.g., shampoo, conditioner). In addition to the PLP, water and optionally, a water-miscible solvent, these types of cosmetic compositions typically contain at least one other cosmetic ingredient, including for example, a hydrophilic gelling agent.

Emulsions

Thus, in addition to the PLP and the solvent, the emulsion will contain at least one other phase e.g., a fatty or oil phase (that typically contains a liquid fatty phase and/or a fatty substance that is at least partially solid at room temperature (20° C.-25° C.)), and/or an aqueous phase (including water), and an emulsifier or other cosmetic ingredient with emulsifying properties (e.g., a self-emulsifying wax), collectively referred to as "emulsifiers". Representative examples of these types of cosmetic compositions include creams, mascara and various hair care products. Aside from specific types of products mentioned above, hair care products that may be formulated in accordance with one of more of the above categories include pre-treatments and post-treatments for color protection, conditioning or protection from heat damage, leave-in hair treatments, rinse-off hair treatments, styling products (e.g., gels, creams, hair lotions, mousses, sprays and waxes), combination shampoo/styling compositions and hair volumizing compositions.

The cosmetic compositions of the present invention may also contain at least one further ingredient, which to the extent they are not already mentioned in connection with any category of composition, representative examples of which include colorants, photoprotective agents (e.g., U.V. filters), secondary film-formers, fillers, cosmetically active agents, and/or cosmetic additives or adjuvant. These ingredients are selected based on several factors, including for example, their compatibility with the PLP and the solvent system, and the intended overall effect of the composition.

Representative examples of all the forementioned cosmetic ingredients are provided below.

Depending upon the nature of the cosmetic composition, the PLP will be formulated with at least one aqueous or non-aqueous polar solvent.

Thus, aside from water, the PLPs of the invention are soluble in water-miscible or at least partially water-miscible compounds, such as polyols or lower C2 to C8 monoalcohols, such as ethanol and isopropanol. "Polyol" should be understood as meaning any organic molecule comprising at least two free hydroxyl groups, examples of which include glycols, such as hexylene glycol, pentylene glycol, butylene glycol, propylene glycol, isoprene glycol, glycerol and polyethylene glycols, such as PEG-8, sorbitol and sugars. In addition to water-miscible solvents, other non-aqueous polar solvents in which the PLPs are soluble include esters (e.g., ethyl 3-ethoxypropionate and isohexyl neopentanoate), fatty alcohols, and fatty esters.

Fatty alcohols that may be useful in the present invention typically contain about 8 to 60 carbon atoms. A fatty alcohol comprising from 8 to 60 carbon atoms is any pure, saturated or unsaturated, branched or unbranched alcohol that comprises from 10 to 40 carbon atoms. Examples of fatty alcohols include linear or branched fatty alcohols of synthetic origin or else of natural origin. Preferred are fatty alcohols containing from 10 to 36 carbon atoms, preferably from 10 to 34 carbon atoms and more preferably from 12 to 32 carbon atoms. Representative examples of fatty alcohols which may be useful in the present invention include octyl dodecanol, lauryl alcohol, myristyl alcohol, cetyl alcohol, stearyl alcohol, isostearyl alcohol, palmityl alcohol, oleyl alcohol, and cetearyl alcohol (which is a mixture of cetyl alcohol and stearyl alcohol).

Ester-based solvents include synthetic esters which may be represented by the formula R1COOR2, in which R1 represents a linear or branched fatty acid residue containing from 1 to 40 carbon atoms and R2 represents a hydrocarbon-based chain, which is for example branched, containing from 1 to 40 carbon atoms. The esters may be chosen for example from esters of fatty acids such as cetostearyl octanoate, isopropyl alcohol esters such as isopropyl myristate, isopropyl palmitate, ethyl palmitate, 2-ethylhexyl palmitate, isopropyl stearate or isostearate, isostearyl isostearate, octyl stearate; hydroxylated esters such as instance isostearyl lactate, octyl hydroxystearate, heptanoates such as isostearyl heptanoate; alcohol or polyalcohol octanoates, decanoates or ricinoleates such as propylene glycol dioctanoate, cetyl octanoate, tridecyl octanoate; C12 to C15 alkyl benzoates; hexyl laurate; neopentanoic acid esters, for instance isodecyl neopentanoate, isotridecyl neopentanoate, isostearyl neopentanoate, octyldodecyl neopentanoate and isohexyl neopentanoate; isononanoic acid esters, for instance isononyl isononanoate, isotridecyl isononanoate, octyl isononanoate; and propionic acid esters such as ethyl 3-ethoxypropionate. The PLP may also be solubilized in an oil as described elsewhere herein in the subsection "Fatty Phase Ingredients".

The amount of solvent(s) present in the composition will vary widely, depending in part on the type of composition in which the PLP is formulated. In general, the amount of solvent ranges from about 1% to about 95%, and in some embodiments from about 1% to about 85% by weight, based on the total weight of the composition.

Structuring Agents

The function of this ingredient is to structure (that is, thicken and/or increase the viscosity of) the product, and particularly an oil phase thereof, in order to form a solid product. Structuring agents that may be useful in the present invention include polyorganosiloxane-containing polymers, non-silicone-polyamide copolymers, waxes, and mixtures thereof. Polyorganosiloxane-containing polymers can generally be described as polymers chosen from homopolymers and copolymers, preferably, with a weight-average molecular mass ranging from about 500 to about $2.5 \times 10^6$ or more, comprising at least one moiety comprising: at least one polyorganosiloxane group comprising, preferably, from 1 to about 10,000 organosiloxane units in the chain of the moiety or in the form of a graft, and at least two groups capable of establishing hydrogen interactions are provided. Polyamides suitable for use herein include any polyamides known in the art. Examples of suitable polyamides include Ester-Terminated PolyAmides (ETPAs), Tertiary-Amide-Terminated PolyAmides (ATPAs), Ester-Terminated PolyEster-Amides (ETPEAs), Tertiary Amide-Terinated PolyEster-Amides (ATPEA), PolyAlkyleneOxy-terminated PolyAmides (PAOPAs), and PolyEther-PolyAmides (PEPAs). Representative examples of these polyamides are listed in U.S. Patent Publication No. 20060229222. Such non-silicone polyamides are commercially available, for instance, from Arizona Chemical Company, Jacksonville, Fla., under the tradenames Uniclear and Sylvaclear. Representative examples of ester terminated polyamides are Uniclear 80 and 100VG. A representative example of a tertiary amide-terminatedpolyamide is Sylvaclear A200, and a representative example of a polyalkyleneoxy terminated polyester is Sylvaclear AF1900.

Suitable waxes are those generally used in cosmetics and dermatology. Representative examples of waxes include those of natural animal, plant or mineral origin, for instance beeswax, carnauba wax, candelilla wax, ouricury wax, Japan wax, cork fiber wax, sugar cane wax, paraffin wax, lignite wax, microcrystalline waxes, lanolin wax, montan wax, ozokerites and hydrogenated oils such as hydrogenated jojoba oil as well as waxes of synthetic origin, for instance polyethylene waxes derived from the polymerization of ethylene, waxes obtained by Fischer-Tropsch synthesis, fatty acid esters and glycerides that are solid at 40° C., for example, at above 55° C., silicone waxes such as alkyl- and alkoxy-poly(di)methyl-siloxanes and/or poly(di)methyl-siloxanes esters that are solid at 40° C., for example, at above 55° C. Waxes approved for food use include ozokerite, rice wax and the waxes referenced in the Codex alimentary.

In general, the amount of structuring agent ranges from about 0.1% to about 60% and in some embodiments from about 0.5% to about 50% by weight, based on the total weight of the composition.

Gelling Agents

These ingredients also referred to as gellants, thickeners or thickening agents, may be hydrophobic (and if water is present, hydrophilic) in nature. Representative examples of oil- or fatty-phase-compatible thickeners that may be suitable for use in the present invention may be polymeric or mineral-based. The thickener may cause gelling via chemical reticulation and agents that gel via physical reticulation. Modified clays may be used as thickeners, including hectorites modified with an ammonium chloride of a C10 to C22 fatty acid, such as hectorite modified with distearyldimethylammonium chloride, also known as quaternium-18 bentonite, such as the products commercially available from Rheox under the tradename Bentone 34, or from Southern Clay under the tradenames Claytone XL, Claytone 34 and Claytone 40, the modified clays known as quaternium-18 benzalkonium bentonites and commercially available from Southern Clay under the tradenames Claytone HT, Claytone GR and Claytone PS, the clays modified with stearyldimethylbenzoylammonium chloride, known as stearalkonium bentonites, such as those commercially available from Southern Clay under the tradenames Claytone APA and Claytone AF, and from Rheox under the tradename Baragel 24. Other mineral thickeners include silica, such as fumed silica.

Representative examples of hydrophilic or aqueous-compatible thickeners that may be useful in the present invention include polysaccharides and gums, e.g., natural gums, xanthan gum, sclerotium, carrageenan and pectin; polysaccharide resins such as starch and its derivatives, for example tapioca starch, polyvinylpyrrolidone (PVP), polyvinyl alcohol, crosslinked polyacrylic acids and acrylates (e.g., Carbopol 982), hydrophobically-modified acrylates (e.g., Carbopol 1382); polyacrylamides such as, for example, the crosslinked copolymers sold under the names Sepigel 305 (CTFA name: polyacrylamide/C13-C14 isoparaffin/Laureth 7) and Simulgel 600 (CTFA name: acrylamide/sodium acryloyldimethyltaurate copolymer/isohexadecane/polysorbate 80) by SEPPIC; 2-acrylamido-2-methylpropanesulphonic acid polymers and copolymers, that are optionally crosslinked and/or neutralized; cellulose derivatives such as hydroxyethylcellulose, sodium carboxymethylcellulose, hydroxypropyl methylcellulose, hydroxypropyl cellulose, ethyl cellulose and hydroxymethyl cellulose; hyaluronic acid and its salts, clays such as montmorillonites, hectorites, bentonites, and laponites, polyglyceryl (meth)acrylates polymers commercially available from Hispano Quimica or Guardian under the tradenames "Hispagel" and "Lubragel", crosslinked acrylamide polymers and copolymers, such as those commercially available from Hoechst under the tradenames "PAS 5161" and "Bozepol C", and crosslinked methacryloyloxyethyltrimethylammonium chloride homopolymers such as those commercially available from Allied Colloid under the tradename "Salcare S.C.95".

The gelling agent or thickener is typically present in an amount ranging from about 0.01% to about 10% by weight, in some embodiments from about 0.1% to about 5% by weight, based on the total weight of the composition.

Powders/Fillers

These ingredients may be obtained from various sources (e.g., mineral or organic), and have any number of shapes (e.g., lamellar or spherical). Representative examples of fillers/powders that may be useful in the present invention include polyamide (Nylon) particles and especially the microbeads sold under the tradename Orgasol by the company Atochem, or nylon fibres; polyethylene powders; microspheres based on acrylic copolymers, such as those made of ethylene glycol dimethacrylate/lauryl methacrylate copolymer sold by the company Dow Corning under the tradename Polytrap; the polymethyl methacrylate microspheres sold under the tradename Microsphere M-100 by the company Matsumoto or under the tradename Covabead LH 85 by the company Wackherr; melamine-formaldehyde or urea-formaldehyde resin particles; poly(tetrafluoroethylene) particles; ethylene-acrylate copolymer powders, for instance those sold under the tradename Flobeads by the company Sumitomo Seika Chemicals; expanded powders such as hollow microspheres and especially microspheres formed from a terpolymer of vinylidene chloride, acrylonitrile and methacrylate, and sold under the tradename Expancel by the company Kemanord Plast under the references 551 DE 12 (particle size of about 12 µm and mass of a unit volume of 40 kg/m$^3$), 551 DE 20 (particle size of about 30 µm and mass of a unit volume of 65 kg/m$^3$) and 551 DE 50 (particle size of about 40 µm), or the polyacrylonitrile microspheres sold under the tradename Micropearl F 80 ED by the company Matsumoto; powders of natural organic materials such as starch powders, especially of crosslinked or non-crosslinked maize, wheat or rice starch, such as the powders of starch crosslinked with octenylsuccinate anhydride, sold under the tradename Dry-Flo by the company National Starch, and cellulose microbeads; and silicone resin microbeads, such as those sold under the tradename Tospearl by the company Toshiba Silicone, especially Tospearl 240.

The amount of filler/powder generally ranges from about 0.1% to about 25% and in some embodiments from about 1% to about 20% by weight, based on the total weight of the composition.

Fatty Phase Ingredients

In addition to the non-aqueous solvent, at least one cosmetically or dermatologically acceptable and, in general, physiologically acceptable oil may be present. As used herein, the term "oil" means any fatty substance that is in liquid form at room temperature and atmospheric pressure. Oils that may be suitable for use in the present invention include both volatile and nonvolatile oils.

The volatile or nonvolatile oils are typically selected from hydrocarbon-based oils, silicone oils, and fluoro oils. The term "hydrocarbon-based oil" refers to oil mainly containing hydrogen and carbon atoms and possibly oxygen, nitrogen, sulfur and/or phosphorus atoms.

Representative categories of non-volatile hydrocarbon-based oils include fatty acids, linear or branched hydrocarbons of plant, mineral, or plant origin, and synthetic oils such as esters and ethers, fatty alcohols and fatty amides.

Examples of fatty acids include caprylic acid, capric acid, lauric acid, myristic acid, palmitic acid, stearic acid, oleic acid, ricinoleic acid, linoleic acid, linolenic acid, arachidic acid, gadoleic acid, behenic acid, erucic acid, brassidic acid, cetoleic acid, lignoceric acid and nervonic acid.

Examples of linear or branched hydrocarbons of mineral origin include mineral oils (e.g., paraffin), petroleum jelly, polydecenes, hydrogenated polyisobutene such as Parleam, perhydrosqualene and squalane.

Examples of hydrocarbon-based plant oils include triglycerides consisting of fatty acid esters of glycerol, the fatty acids of which may have chain lengths ranging from C4 to C24, these chains possibly being linear or branched, and saturated or unsaturated, e.g., heptanoic or octanoic triglycerides, groundnut oil, babassu oil, coconut oil, grapeseed oil, cottonseed oil, corn oil, corn germ oil, mustard seed oil, palm oil, rapeseed oil, sesame seed oil, soybean oil, sunflower oil, wheatgerm oil, canola oil, apricot oil, mango oil, castor oil, shea oil, avocado oil, olive oil, sweet almond oil, peach kernel oil, walnut oil, hazelnut oil, macadamia oil, jojoba oil, alfalfa oil, poppy seed oil, pumpkin oil, marrow oil, blackcurrant seed oil, evening primrose oil, millet oil, barley oil, quinoa oil, rye oil, safflower oil, candlenut oil, passionflower oil, musk rose oil or shea butter oil and alternatively caprylic/capric acid triglycerides.

Representative examples of synthetic esters and ethers, in particular of fatty acids, such as oils of formulae R1COOR2 and R1 OR2 in which R1 represents the residue of a fatty acid or of a fatty alcohol comprising from 8 to 29 carbon atoms and R2 represents a branched or unbranched hydrocarbon chain comprising from 3 to 30 carbon atoms, such as, for example, purcellin oil, octyl palmitate, isopropyl lanolate, 2-octyldodecyl stearate, 2-octyldodecyl erucate or isostearyl isostearate; hydroxylated esters, such as isostearyl lactate, octyl hydroxystearate, octyldodecyl hydroxystearate, diisostearyl malate, triisocetyl citrate or heptanoates, octanoates or decanoates of fatty alcohols; polyol esters, such as propylene glycol dioctanoate, neopentyl glycol diheptanoate and diethylene glycol diisononanoate; and pentaerythritol esters, such as pentaerythrityl tetraisostearate; or lipophilic derivatives of amino acids, such as isopropyl lauroyl sarcosinate (INCI name). Yet other examples include $C_{12}$-$C_{15}$ alkyl benzoates such as those sold under the tradenames "Finsolv TN" and "Witconol TN" by the company Witco, and 2-ethylphenyl benzoate, for instance the product sold under the name X-TEND 226® by the company ISP, triglycerides such as dicaprylyl carbonate (e.g., Cetiol CC, sold by Cognis), and oxyethylenated or oxypropylenated fatty esters and ethers.

Fatty alcohols which may be useful in the present invention tend to be liquid at room temperature and have a branched and/or unsaturated carbon-based chain containing from 12 to 26 carbon atoms. Representative examples thus include 2-octyldodecanol, isostearyl alcohol, oleyl alcohol, 2-hexyldecanol, 2-butyloctanol and 2-undecylpentadecanol.

Representative examples of fatty amides include isopropyl lauroyl sarcosinate such as the product sold under the tradename "Eldew SL-205" by the company Ajinomoto).

Representative examples of volatile hydrocarbon-based oils include oils containing from 8 to 16 carbon atoms, and especially branched C8-C16 alkanes (also known as isoparaffins), for instance isododecane (also known as 2,2,4,4,6-pentamethylheptane), isodecane and isohexadecane.

Examples of nonvolatile silicone oils that may be useful in the present invention include nonvolatile polydimethylsiloxanes (PDMS), polydimethylsiloxanes comprising alkyl or alkoxy groups that are pendent and/or at the end of a silicone chain, these groups each containing from 2 to 24 carbon atoms, phenyl silicones, for instance phenyl trimethicones, phenyl dimethicones, phenyl trimethylsiloxy diphenylsiloxanes, diphenyl dimethicones, diphenyl methyldiphenyl trisiloxanes and 2-phenylethyl trimethylsiloxysilicates, and dimethicones or phenyltrimethicones with a viscosity of less than or equal to 100 cSt.

Representative examples of volatile silicone oils that may be useful in the present invention include volatile linear or cyclic silicone oils, especially those with a viscosity ≤8 centistokes ($8 \times 10^{-6}$ m²/s) and especially containing from 2 to 10 silicon atoms and in particular from 2 to 7 silicon atoms, these silicones optionally comprising alkyl or alkoxy groups containing from 1 to 10 carbon atoms. Specific examples include dimethicones with a viscosity of 5 and 6 cSt, octamethylcyclotetrasiloxane, decamethylcyclopentasiloxane, dodecamethylcyclohexasiloxane, heptamethylhexyltrisiloxane, heptamethyloctyltrisiloxane, hexamethyldisiloxane, octamethyltrisiloxane, decamethyltetrasiloxane and dodecamethylpentasiloxane, and mixtures thereof.

Representative examples of volatile fluoro oils that may be suitable for use in the present invention include nonafluoromethoxybutane and perfluoro-methylcyclopentane.

The amount of oil that may present in the compositions generally ranges from about 5% to about 99% and in some embodiments, from about 10% to about 80% by weight, based on the total weight of the composition.

The fatty phase may contain any other standard fat-soluble or fat/oil-dispersible additive such as waxes and other polymeric structuring agents, and pasty compounds or substances, which as used herein, refer to fatty compounds with a reversible solid/liquid change of state and containing, at a temperature of 25° C., a liquid fraction and a solid fraction. Examples of pasty compounds, such as polyol esters, are described in U.S. Patent Application Publication 2010/0015074 A1.

The amount of fatty phase (including both liquids and solids), exclusive of emulsifier and hydrophobic gelling agent, that may present in the compositions generally ranges from about 5% to about 80% and in some embodiments, from about 10% to about 50% by weight, based on the total weight of the composition.

Emulsifier

Representative examples of emulsifiers that may be particularly suitable for use in the present invention include non-ionic amphiphilic lipids and anionic amphiphilic lipids.

Nonionic Amphiphilic Lipids:

The nonionic amphiphilic lipids of the invention are preferably chosen from 1) silicone surfactants; 2) amphiphilic lipids that are fluid at a temperature of less than or equal to 45° C., chosen from the esters of at least one polyol chosen from the group formed by polyethylene glycol comprising from 1 to 60 ethylene oxide units, sorbitan, glycerol comprising from 2 to 30 ethylene oxide units, polyglycerols comprising from 2 to 15 glycerol units, and of at least one fatty acid comprising at least one saturated or unsaturated, linear or branched $C_8$-$C_{22}$ alkyl chain; 3) mixed esters of fatty acid or of fatty alcohol, of carboxylic acid and of glycerol; 4) fatty acid esters of sugars and fatty alcohol ethers of sugars; 5) surfactants that are solid at a temperature of less than or equal to 45° C., chosen from fatty esters of glycerol, fatty esters of sorbitan and oxyethylenated fatty esters of sorbitan, ethoxylated fatty ethers and ethoxylated fatty esters; and 6) block copolymers of ethylene oxide (A) and of propylene oxide (B).

The silicone surfactants which can be used according to the invention are silicone compounds comprising at least one oxyethylene chain —OCH₂CH₂— and/or oxypropylene chain —OCH₂CH₂CH₂—. As silicone surfactants which can be used according to the present invention, mention may be made of those disclosed in documents U.S. Pat. No. 5,364,633 and U.S. Pat. No. 5,411,744.

The silicone surfactant used according to the present invention is preferably a compound of formula (I):

in which:

$R_1$, $R_2$ and $R_3$, independently of each other, represent a $C_1$-$C_6$ alkyl radical or a radical —$(CH_2)_x$—$(OCH_2CH_2)_y$—$(OCH_2CH_2CH_2)_z$—$OR_4$, at least one radical $R_1$, $R_2$ or $R_3$ not being an alkyl radical; $R_4$ being a hydrogen, an alkyl radical or an acyl radical; A is an integer ranging from 0 to 200; B is an integer ranging from 0 to 50; with the proviso that A and B are not simultaneously equal to zero; x is an integer ranging from 1 to 6; y is an integer ranging from 1 to 30; and z is an integer ranging from 0 to 5.

According to one preferred embodiment of the invention, in the compound of formula (I), the alkyl radical is a methyl radical, x is an integer ranging from 2 to 6 and y is an integer ranging from 4 to 30.

As examples of silicone surfactants of formula (I), mention may be made of the compounds of formula (II):

(II)

in which A is an integer ranging from 20 to 105, B is an integer ranging from 2 to 10 and y is an integer ranging from 10 to 20.

As examples of silicone surfactants of formula (I), mention may also be made of the compounds of formula (III):

(III)

in which A' and y are integers ranging from 10 to 20.

Compounds of the invention which may be used are those sold by the company Dow Corning under the names DC 5329, DC 7439-146, DC 2-5695 and Q4-3667. The compounds DC 5329, DC 7439-146 and DC 2-5695 are compounds of formula (II) in which, respectively, A is 22, B is 2 and y is 12; A is 103, B is 10 and y is 12; A is 27, B is 3 and y is 12.

The compound Q4-3667 is a compound of formula (III) in which A is 15 and y is 13.

The amphiphilic lipids that are fluid at a temperature of less than or equal to 45° C. are, in particular: the isostearate of polyethylene glycol of molecular weight 400, sold under the name PEG 400 by the company Unichema; diglyceryl isostearate, sold by the company Solvay; glyceryl laurate comprising 2 glycerol units, sold by the company Solvay; sorbitan oleate, sold under the name Span 80 by the company ICI; sorbitan isostearate, sold under the name Nikkol SI 10R by the company Nikko; and α-butylglucoside cocoate or α-butylglucoside caprate, sold by the company Ulice.

The mixed esters of fatty acid or of fatty alcohol, of carboxylic acid and of glycerol, which can be used as surfactants in the cosmetic composition according to the invention, may be chosen in particular from the group comprising mixed esters of fatty acid or of fatty alcohol with an alkyl chain containing from 8 to 22 carbon atoms, and of α-hydroxy acid and/or of succinic acid, with glycerol. The α-hydroxy acid may be, for example, citric acid, lactic acid, glycolic acid or malic acid, and mixtures thereof.

The alkyl chain of the fatty acids or alcohols from which are derived the mixed esters which can be used in the cosmetic composition of the invention may be linear or branched, and saturated or unsaturated. They may especially be stearate, isostearate, linoleate, oleate, behenate, arachidonate, palmitate, myristate, laurate, caprate, isostearyl, stearyl, linoleyl, oleyl, behenyl, myristyl, lauryl or capryl chains, and mixtures thereof.

As examples of mixed esters which can be used in the cosmetic composition of the invention, mention may be made of the mixed ester of glycerol and of the mixture of citric acid, lactic acid, linoleic acid and oleic acid (CTFA name: Glyceryl citrate/lactate/linoleate/oleate) sold by the company Hills under the name Imwitor 375; the mixed ester of succinic acid and of isostearyl alcohol with glycerol (CTFA name: Isostearyl diglyceryl succinate) sold by the company Hills under the name Imwitor 780 K; the mixed ester of citric acid and of stearic acid with glycerol (CTFA name: Glyceryl stearate citrate) sold by the company Hills under the name Imwitor 370; the mixed ester of lactic acid and of stearic acid with glycerol (CTFA name: Glyceryl stearate lactate) sold by the company Danisco under the name Lactodan B30 or Rylo LA30.

Fatty acid esters of sugars, which can be used as surfactants in the cosmetic composition according to the invention, are preferably solid at a temperature of less than or equal to 45° C. and may be chosen in particular from the group comprising esters or mixtures of esters of $C_8$-$C_{22}$ fatty acid and of sucrose, of maltose, of glucose, or of fructose, and esters or mixtures of esters of $C_{14}$-$C_{22}$ fatty acid and of methylglucose.

The $C_8$-$C_{22}$ or $C_{14}$-$C_{22}$ fatty acids forming the fatty unit of the esters which can be used in the cosmetic composition of the invention comprise a saturated or unsaturated linear alkyl chain containing, respectively, from 8 to 22 or from 14 to 22 carbon atoms. The fatty unit of the esters may be chosen in particular from stearates, behenates, arachidonates, palmitates, myristates, laurates and caprates, and mixtures thereof. Stearates are preferably used.

As examples of esters or mixtures of esters of fatty acid and of sucrose, of maltose, of glucose or of fructose, mention may be made of sucrose monostearate, sucrose distearate and sucrose tristearate and mixtures thereof, such as the products sold by the company Croda under the name Crodesta F50, F70, F110 and F160 having, respectively, an HLB (hydrophilic lipophilic balance) of 5, 7, 11 and 16; and examples of esters or mixtures of esters of fatty acid and of methylglucose which may be mentioned are methylglucose polyglyceryl-3 distearate, sold by the company Goldschmidt under the name Tego-care 450. Mention may also be made of glucose or maltose monoesters such as methyl o-hexadecanoyl-6-D-glucoside and o-hexadecanoyl-6-D-maltoside.

The fatty alcohol ethers of sugars, which can be used as surfactants in the cosmetic composition according to the invention, are solid at a temperature of less than or equal to 45° C. and may be chosen in particular from the group comprising ethers or mixtures of ethers of $C_8$-$C_{22}$ fatty alcohol and of glucose, of maltose, of sucrose or of fructose, and ethers or mixtures of ethers of a $C_{14}$-$C_{22}$ fatty alcohol and of methylglucose. These are in particular alkylpolyglucosides.

The $C_8$-$C_{22}$ or $C_{14}$-$C_{22}$ fatty alcohols forming the fatty unit of the ethers which may be used in the cosmetic composition of the invention comprise a saturated or unsaturated, linear alkyl chain containing, respectively, from 8 to 22 or from 14 to 22 carbon atoms. The fatty unit of the ethers may be chosen in particular from decyl, cetyl, behenyl, arachidyl, stearyl, palmityl, myristyl, lauryl, capryl and hexadecanoyl units, and mixtures thereof, such as cetearyl.

As examples of fatty alcohol ethers of sugars, mention may be made of alkylpolyglucosides such as decylglucoside and laurylglucoside, which is sold, for example, by the company Henkel under the respective names Plantaren 2000 and Plantaren 1200, cetostearyl glucoside optionally as a mixture with cetostearyl alcohol, sold for example, under the name Montanov 68 by the company SEPPIC, under the name Tego-care CG90 by the company Goldschmidt and under the name Emulgade KE3302 by the company Henkel, as well as arachidyl glucoside, for example in the form of a mixture of arachidyl alcohol and behenyl alcohol and arachidyl glucoside, sold under the name Montanov 202 by the company SEPPIC.

The surfactant used more particularly is sucrose monostearate, sucrose distearate or sucrose tristearate and mixtures thereof, methylglucose polyglyceryl-3 distearate and alkylpolyglucosides.

The fatty esters of glycerol which may be used as surfactants in the cosmetic composition according to the invention, which are solid at a temperature of less than or equal to 45° C., may be chosen in particular from the group comprising esters formed from at least one, acid comprising a saturated linear alkyl chain containing from 16 to 22 carbon atoms and from 1 to 10 glycerol units. One or more of these fatty esters of glycerol may be used in the cosmetic composition of the invention.

These esters may be chosen in particular from stearates, behenates, arachidates and palmitates, and mixtures thereof. Stearates and palmitates are preferably used.

As examples of surfactants which can be used in the cosmetic composition of the invention, mention may be made of decaglyceryl monostearate, distearate, tristearate and pentastearate (CTFA names: Polyglyceryl-10 stearate, Polyglyceryl-10 distearate, Polyglyceryl-10 tristearate, Polyglyceryl-10 pentastearate), such as the products sold under the respective names Nikkol Decaglyn 1-S, 2-S, 3-S and 5-S by the company Nikko, and diglyceryl monostearate (CTFA name: Polyglyceryl-2 stearate), such as the product sold by the company Nikko under the name Nikkol DGMS.

The fatty esters of sorbitan which may be used as surfactants in the cosmetic composition according to the invention are solid at a temperature of less than or equal to 45° C. and are chosen from the group comprising $C_{16}$-$C_{22}$ fatty acid esters of sorbitan and oxyethylenated $C_{16}$-$C_{22}$ fatty acid esters of sorbitan. They are formed from at least one fatty acid comprising at least one saturated linear alkyl chain containing, respectively, from 16 to 22 carbon atoms, and from sorbitol or from ethoxylated sorbitol. The oxyethylenated esters generally comprise from 1 to 100 ethylene glycol units and preferably from 2 to 40 ethylene oxide (EO) units.

These esters may be chosen in particular from stearates, behenates, arachidates, palmitates, and mixtures thereof. Stearates and palmitates are preferably used.

As examples of surfactants which can be used in the cosmetic composition of the invention, mention may be made of sorbitan monostearate (CTFA name: sorbitan stearate), sold by the company ICI under the name Span 60, sorbitan monopalmitate (CTFA name: sorbitan palmitate), sold by the company ICI under the name Span 40, and sorbitan tristearate 20 EO (CTFA name: polysorbate 65), sold by the company ICI under the name Tween 65.

The ethoxylated fatty ethers that are solid at a temperature of less than or equal to 45° C., which may be used as surfactants in the cosmetic composition according to the invention, are preferably ethers formed from 1 to 100 ethylene oxide units and from at least one fatty alcohol chain containing from 16 to 22 carbon atoms. The fatty chain of the ethers may be chosen in particular from behenyl, arachidyl, stearyl and cetyl units, and mixtures thereof, such as cetearyl. Examples of ethoxylated fatty ethers which may be mentioned are behenyl alcohol ethers comprising 5, 10, 20 and 30 ethylene oxide units (CTFA names: beheneth-5, beheneth-10, beheneth-20, beheneth-30), such as the products sold under the names Nikkol BBS, BB10, BB20 and BB30 by the company Nikko, and stearyl alcohol ether comprising 2 ethylene oxide units (CTFA name: steareth-2), such as the product sold under the name Brij 72 by the company ICI.

The ethoxylated fatty esters that are solid at a temperature of less than or equal to 45° C., which may be used as surfactants in the cosmetic composition according to the invention, are esters formed from 1 to 100 ethylene oxide units and from at least one fatty acid chain containing from 16 to 22 carbon atoms. The fatty chain in the esters may be chosen in particular from stearate, behenate, arachidate and palmitate units, and mixtures thereof. Examples of ethoxylated fatty esters which may be mentioned are the ester of stearic acid comprising 40 ethylene oxide units, such as the product sold under the name Myrj 52 (CTFA name: PEG-40 stearate) by the company ICI, as well as the ester of behenic acid comprising 8 ethylene oxide units (CTFA name: PEG-8 behenate), such as the product sold under the name Compritol HD5 ATO by the company Gattefosse.

The block copolymers of ethylene oxide (A) and of propylene oxide (B), which may be used as surfactants in the cosmetic composition according to the invention, may be chosen in particular from block copolymers of formula (IV):

$$HO(C_2H_4O)x(C_3H_6O)y(C_2H_4O)zH \qquad (IV)$$

in which x, y and z are integers such that x+z ranges from 2 to 100 and y ranges from 14 to 60, and mixtures thereof, and more particularly from the block copolymers of formula (IV) having an HLB value ranging from 2 to 16.

These block copolymers may be chosen in particular from poloxamers and in particular Poloxamer 231, such as the product sold by the company ICI under the name Pluronic L81 of formula (IV) in which x=z=6, y=39 (HLB 2); Poloxamer 282, such as the product sold by the company ICI under the name Pluronic L92 of formula (IV) in which x=z=10, y=47 (HLB 6); and Poloxamer 124, such as the product sold by the company ICI under the name Pluronic L44 of formula (IV) in which x=z=11, y=21 (HLB 16).

Among the nonionic amphiphilic lipids that are preferably used are polyethylene glycol isostearate (8 mol of ethylene oxide), diglyceryl isostearate, polyglyceryl monolaurate and monostearate comprising 10 glycerol units, sorbitan oleate, and sorbitan isostearate.

Anionic Amphiphilic Lipids:

The anionic amphiphilic lipids of the invention are chosen in particular from Alkyl ether citrates, Alkoxylated alkenyl succinates, Alkoxylated glucose alkenyl succinates, and Alkoxylated methylglucose alkenyl succinates.

The alkyl ether citrates which may be used as surfactants in the cosmetic composition according to the invention may be chosen in particular from the group comprising monoesters, diesters or triesters formed from citric acid and from at least one oxyethylenated fatty alcohol comprising a linear or branched, saturated or unsaturated alkyl chain containing from 8 to 22 carbon atoms, and comprising from 3 to 9 ethoxylated groups, and mixtures thereof. Specifically, it is possible to use a mixture of one or more of these citrates in the cosmetic composition of the invention.

These citrates may be chosen, for example, from the mono-, di- and triesters of citric acid and of ethoxylated lauryl alcohol, comprising from 3 to 9 ethoxylated groups, which are sold by the company Witco under the name Witconol EC, in particular Witconol EC 2129 which is predominantly a dilaureth-9 citrate, and Witconol EC 3129 which is predominantly a trilaureth-9 citrate.

The alkyl ether citrates used as surfactants are preferably used in a form neutralized to a pH of about 7, the neutralizing agent being chosen from inorganic bases such as sodium hydroxide, potassium hydroxide or ammonia, and organic bases such as monoethanolamine, diethanolamine, triethanolamine, 1,3-aminomethylpropanediol, N-methylglucamine, basic amino acids such as arginine and lysine, and mixtures thereof.

The alkenyl succinates which may be used as surfactants in the cosmetic composition of the invention are, in particular, ethoxylated and/or propoxylated derivatives and they are preferably chosen from the compounds of formula (V) or (VI):

HOOC—(HR)C—CH$_2$—COO-E      (V)

HOOC—(HR)C—CH$_2$—COO-E-O—CO—CH$_2$—C(HR')—COOH      (VI)

in which the radicals R and R' are chosen from linear or branched alkenyl radicals containing from 6 to 22 carbon atoms, and E is chosen from oxyethylene chains of formula $(C_2H_4O)_n$ in which n ranges from 2 to 100, oxypropylene chains of formula $(C_3H_6O)_{n'}$ in which n' ranges from 2 to 100, random or block copolymers comprising oxyethylene chains of formula $(C_2H_{40})_n$ and oxypropylene chains of formula $(C_3H_6O)_{n'}$ such that the sum of n and n' ranges from 2 to 100, the oxyethylenated and/or oxypropylenated glucose groups comprising on average. from 4 to 100 oxyethylene and/or oxypropylene units distributed on all the hydroxyl functions, the oxyethylenated and/or oxypropylenated methylglucose groups comprising on average from 4 to 100 oxyethylene and/or oxypropylene units distributed on all the hydroxyl functions.

In formulae (V) and (VI), n and n' are average values and are thus not necessarily integers. A value of n ranging from 5 to 60 and even more preferably from 10 to 30 is advantageously chosen.

The radical R and/or R' is advantageously chosen from linear alkenyl radicals containing from 8 to 22 and preferably from 14 to 22 carbon atoms. It may be, for example, the hexadecenyl radical containing 16 carbon atoms or the octadecenyl radical containing 18 carbon atoms.

The compounds of formulae (V) and (VI) described above, in which E is chosen from oxyethylene chains, oxypropylene chains and copolymers comprising oxyethylene chains and oxypropylene chains, may be prepared in accordance with the description given in documents WO-A-94/00508, EP-A-107199 and GB-A-2 131 820.

The acid function —COOH in the surfactants of formulae (V) and (VI) is generally in the cosmetic composition of the invention in a form which is neutralized with a neutralizing agent, the neutralizing agents being chosen, for example, from inorganic bases such as sodium hydroxide, potassium hydroxide or ammonia, and organic bases such as monoethanolamine, diethanolamine, triethanolamine, 1,3-aminomethylpropanediol, N-methylglucamine, basic amino acids such as arginine and lysine, and mixtures thereof.

As examples of surfactants which can be used in the cosmetic composition of the invention, mention may be made of hexadecenyl succinate 18 EO (compound of formula V with R=hexadecenyl, E=$(C_2H_4O)_n$, n=18), hexadecenyl succinate 45 EO (compound of formula V with R=hexadecenyl, E=$(C_2H_4O)_n$, n=45), dihexadecenyl succinate 18 EO (compound of formula VI with R=R'=hexadecenyl, E=$(C_2H_4O)_n$, n=18), dihexadecenyl glucose succinate 10 EO (compound of formula VI with R'R'=hexadecenyl, E=oxyethylenated glucose containing 10 oxyethylene groups), dihexadecenyl glucose succinate 20 EO (compound of formula VI with R=R'=hexadecenyl, E=oxyethylenated glucose containing 20 oxyethylene groups), dioctadecenyl methylglucose succinate 20 EO (compound of formula VI with R=R'=octadecenyl, E=oxyethylenated methylglucose containing 20 oxyethylene groups), and mixtures thereof.

Depending on its more hydrophilic or more lipophilic nature, the nonionic or anionic amphiphilic lipid may be introduced into the aqueous phase or into the oily phase of the cosmetic composition.

Other Emulsifiers:

Cationic and amphoteric emulsifiers may also be useful.

Emulsifiers may be present even in inventive cosmetic compositions besides emulsions. The amount of emulsifier generally ranges from about 0.1% to about 25% and in some embodiments from about 1% to about 20% by weight, based on the total weight of the composition.

Additional Film-Forming Polymers

These ingredients may be present in the inventive compositions, specifically selected depending on their compatibility with the PLP and the solvent. Broadly, film-forming polymers include synthetic polymers (of the free-radical type or the poly-condensate type), and polymers of natural origin. Of the term "free-radical film-forming polymer," it is meant a polymer obtained by polymerization of unsaturated, e.g., ethylenically unsaturated monomers, capable of homopolymerization. Representative examples of these polymers that may be suitable for use in the present invention include vinyl polymers or copolymers, e.g., acrylic polymers. Vinyl film-forming polymers result from the polymerization of ethylenically unsaturated monomers containing at least one acidic group (e.g., α,β-ethylenic unsaturated carboxylic acids such as acrylic acid, methacrylic acid, crotonic acid, maleic acid, and itaconic acid), esters of the acid monomers (e.g., (meth)acrylates, such as (meth)acrylates of an alkyl, such as a C1-C30 and preferably C1-C20 alkyl, (meth)acrylates of an aryl, such as a C6-C10 aryl, and (meth)acrylates of a hydroxyalkyl, such as a C2-C6 hydroxyalkyl) and amides of the acid monomers (e.g., (meth)acrylamides, including N-alkyl (meth)acrylamides, such as a C2-C12 alkyl such as N-alkyl (meth)acrylamides, N-ethylacrylamide, N-t-butylacrylamide, N-t-octylacrylamide and N-undecylacrylamide). Vinyl film-forming polymers may also result from the homopolymerization or copolymerization of monomers selected from vinyl esters and styrene monomers, or copolymerization wherein these monomers are polymerized with the aforementioned acid, ester or amide monomers.

Representative examples of film-forming polycondensates that may be useful in the present invention include polyurethanes, polyesters, polyesteramides, polyamides, epoxy ester resins and polyureas.

The polymers of natural origin, which may be optionally modified, typically include shellac resin, sandarac gum, dammar resins, elemi gums, copal resins and cellulosic polymers.

Representative examples of specific oil/lipid-soluble film-forming polymers which may be suitable for use in the present invention include polyalkylenes, e.g., polybutene; alkylcelluloses with a linear or branched, saturated or unsaturated C1-C8 alkyl radical, e.g., ethylcellulose and propylcellulose; copolymers of vinylpyrrolidone (VP), e.g., copolymers of VP and C3-C20 alkenes, e.g., VP/vinyl acetate, VP/ethyl methacrylate, VP/eicosene, VP/hexadecene, and VP/styrene. Yet other oil/lipid-soluble film-forming polymers that may be useful include silicone resins, such as cross-linked polyorganosiloxanes and silicone resin copolymers. Block copolymers may also be useful (e.g., film-forming linear block ethylenic polymers which contain at least a first block and at least a second block with different glass transition temperatures that are linked together via an intermediate block containing at least one constituent monomer of the first block and at least one constituent monomer of the second block).

The film-forming polymer may also be present in an inventive composition in the form of particles dispersed in ah aqueous phase (e.g., a (meth)acrylates copolymer) or in a non-aqueous solvent phase, which is generally known as a latex or pseudo latex.

Specific examples of representative polymers, including commercially available film-forming polymers are described in U.S. Patent Application Publication 2010/0278770 A1.

Additional film-forming polymers may be present in amounts generally ranging from about 0.1% to about 50% and in some embodiments from about 0.2% to about 40% by weight, based on the total weight of the composition.

Colorants

Colorants may be chosen from the lipophilic dyes, hydrophilic dyes, traditional pigments, and nacres usually used in cosmetic or dermatological compositions, and mixtures thereof. The coloring agent may have any shape, such as, for example, spheroidal, oval, platelet, irregular, and mixtures thereof. Pigments may optionally be surface-treated e.g., with silicones (e.g., inorganic pigments may be coated with simethicone), perfluorinated compounds, lecithin, and amino acids.

The liposoluble dyes include, for example, Sudan Red, D&C Red 17, D&C Green 6, soybean oil, Sudan Brown, D&C Yellow 11, D&C Violet 2, D&C Orange 5, quinoline yellow and annatto. The water-soluble dyes are, for example, beetroot juice or methylene blue.

The pigments may be chosen from white pigments, colored pigments, inorganic pigments, organic pigments, coated pigments, uncoated pigments, pigments having a micron size and pigments not having a micron size. Among the inorganic pigments that may be mentioned are titanium dioxide, optionally surface-treated, zirconium oxide, zinc oxide, cerium oxide, chromium oxide, manganese violet, ultramarine blue, chromium hydrate, and ferric blue. Among the organic pigments which may be mentioned are carbon black, pigments of D&C type, lakes based on cochineal carmine, lakes based on barium, lakes based on strontium, lakes based on calcium, and lakes based on aluminum.

The nacreous pigments may, for example, be chosen from white nacreous pigments such as mica coated with titanium and mica coated with bismuth oxychloride, colored nacreous pigments such as titanium mica with iron oxides, titanium mica with, for example, ferric blue and/or chromium oxide, titanium mica with an organic pigment of the type mentioned above, as well as nacreous pigments based on bismuth oxychloride, interferential pigments, and goniochromatic pigments.

Colorants, which as taught herein are optional due to the colorizing effect of the PLP, are generally present in an amount ranging from about 0.01% to about 20% and in some embodiments from about 0.1% to about 10%, by weight, based on the total weight of the composition.

Photoprotectants

These ingredients which are also referred to as U.V. filters, can be organic or inorganic (or physical) agents. Representative examples of organic photoprotective agents that may be suitable for use in the present invention include dibenzoylmethane derivatives, e.g., butylmethoxydibenzoylmethane; cinnamic derivatives, e.g., ethylhexyl methoxycinnamate, isopropyl methoxycinnamate, isoamyl methoxycinnamate, DEA methoxycinnamate, diisopropyl methylcinnamate, and glyceryl ethylhexanoate dimethoxycinnamate; para-aminobenzoic acid derivatives, e.g., PABA, ethyl PABA, ethyl dihydroxypropyl PABA, ethylhexyl dimethyl PABA, glyceryl PABA, and PEG-25 PABA; salicylic derivatives, e.g., homosalate, ethylhexyl salicylate, dipropyleneglycol salicylate, and TEA salicylate; β,β-diphenylacrylate derivatives, e.g., octocrylene and etocrylene; benzylidenecamphor derivatives, e.g., 3-benzylidene camphor, 0.4-methylbenzylidene camphor, benzylidene camphor sulfonic acid, camphor benzalkonium methosulfate, terephthalylidene dicamphor sulfonic acid, and polyacrylamidomethyl benzylidene camphor; phenylbenzimidazole derivatives, e.g., phenylbenzimidazole sulfonic acid, and disodium phenyl dibenzimidazole tetrasulfonate; phenylbenzotriazole derivatives, e.g., drometrizole trisiloxane and methylene bis-benzotriazolyl tetramethylbutyl-phenol; triazine derivatives, e.g., bis-ethylhexyloxyphenol methoxyphenyl triazine, ethylhexyl triazone, diethylhexyl butamido triazone, 2,4,6-tris(dineopentyl 4'-aminobenzalmalonate)-s-triazine, 2,4,6-tris(diisobutyl 4'-aminobenzalmalonate)-s-triazine, 2,4-bis(n-butyl 4'-aminobenzoate)-6-(aminopropyl-trisiloxane)-s-triazine, and 2,4-bis(dineopentyl 4'-aminobenzalmalonate)-6-(n-butyl 4'-aminobenzoate)-s-triazine; anthranilic derivatives, e.g., menthyl anthranilate; imidazoline derivatives, e.g., ethylhexyl dimethoxybenzylidene dioxoimidazoline propionate; benzalmalonate derivatives, e.g., polyorganosiloxane comprising benzalmalonate functional groups; 4,4-diarylbutadiene derivatives, e.g., 1,1-dicarboxy(2,2'-dimethylpropyl)-4,4-diphenylbutadiene; benzoxazole derivatives, e.g., 2,4-bis[5-1-(dimethylpropyl)benzoxazol-2-yl-(4-phenyl)imino]-6-(2-ethylhexyl)imino-1,3,5-triazine; and merocyanine derivatives, e.g., octyl 5-(N,N-diethylamino)-2-phenylsulfonyl-2,4-pentadienoate.

Preferred organic photoprotectants include octocrylene, homosalate, butylmethoxydibenzoylmethane, and ethylhexyl methoxycinnamate.

Representative inorganic photoprotectants are typically pigments formed of metal oxides which may or may not be coated (and which typically have a mean particle size between about $5 \times 10^{-3}$ µm and $100 \times 10^{-3}$ µm. Specific examples include pigments formed of titanium oxide, iron oxide, zinc oxide, zirconium oxide, and cerium oxide.

Representative examples of commercially available organic and inorganic photoprotective agents that may be useful in the present invention are disclosed, for example, U.S. Patent Application Publication 2010/0190740 A1.

Photoprotectants are generally present in an amount ranging from about 0.5% to about 50%, and in some embodiments from about 1% to about 40% by weight, based on the total weight of the composition.

Cosmetic Active Agents and Other Additives or Adjuvants

The compositions of the present invention may further contain at least one cosmetically active agent representative examples of which include anti-inflammatory agents, defoaming agents, emollients, vitamins, keratolytic and desquamating agents, α-hydroxy acids, depigmenting agents, salicylic acid, retinoids, hydrocortisone, natural extracts, steroids, anti-bacterial agents, enzymes, flavanoids, soothing agents, mattifying agents, trace elements, and essential fatty acids. Aside from the forementioned fillers/powders, colorants, dispersion agents and photoprotectants, the compositions of the present invention may further contain at least one cosmetic (cosmetically acceptable) additive or adjuvant, representative examples of which include emollients, moisturizers, fibers, preservatives, chelators (such as EDTA and salts thereof, particularly sodium and potassium salts), antioxidants (e.g., BHT, tocopherol), essential oils, fragrances and neutralizing or pH-adjusting agents (e.g., sodium hydroxide). These ingredients may be selected for compatibility with aqueous or non-aqueous solvents (e.g., aqueous or fatty phase).

Cosmetic active agents and other cosmetic additives or adjuvants may present in the compositions in amounts generally ranging from about 0.01% to about 40% and in some embodiments from about 0.05% to about 30% by weight, based on the total weight of the composition.

All publications cited in the specification, both patent publications and non-patent publications are indicative of the level of skill of those skilled in the art to which this invention pertains. All these publications are herein incorporated by reference to the same extent as if each individual publication were specifically and individually indicated as being incorporated by reference.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A cosmetic composition, comprising a) a photoluminescent polymer (PLP) which is a polyester synthesized from a multifunctional monomer containing two carboxylic acid groups and a functional moiety comprising a carboxylic acid group or a hydroxyl group, and a diol, wherein the photoluminescent polymer has grafted thereon or incorporated into the polymer backbone, an amino acid or an amino acid derivative which is S-benzyl-L-cysteine, b) a solvent and c) at least one additional cosmetically acceptable ingredient comprising a structuring agent, a gelling agent, a powder, a filler, an emulsifier, a liquid fatty phase or a combination of two or more thereof, wherein the composition is selected from the group consisting of a non-compressed foundation powder or stick, a compressed foundation powder or stick, a cosmetic paste, mascara, lipstick, lip gloss, lip balm, a cosmetic lotion, a cosmetic cream, and a hair care product.

2. The cosmetic composition of claim 1, wherein the multifunctional monomer comprises citric acid or a derivative thereof which is triethyl citrate.

3. The cosmetic composition of claim 1, wherein the multifunctional monomer further comprises an unsaturated dicarboxylic monomer.

4. The cosmetic composition of claim 3, wherein the unsaturated dicarboxylic monomer is selected from the group consisting of vinyl-containing maleic acid, maleic anhydride, fumaric acid, fumaryl chloride, and acroylchloride.

5. The cosmetic composition of claim 1, wherein the diol comprises a saturated or unsaturated C3-C12 diol.

6. The cosmetic composition of claim 1, wherein the diol is selected from the group consisting of 1,8-octanediol, ethylene diol, propylene diol, poly(ethylene glycol), poly(propylene glycol), 1,3-propanediol, ethanediol, and cis-1,2-cyclohexanediol.

7. The cosmetic composition of claim 1, wherein the amino acid is selected from the group consisting of cysteine, serine, threonine, histidine, phenylalanine, tryptophan and tyrosine, or a derivative thereof which is S-benzyl-L-cysteine.

8. The cosmetic composition of claim 1, wherein the multifunctional monomer comprises citric acid, the diol comprises 1,8-octanediol, and the amino acid is selected from the group consisting of the L-amino acids Alanine (Ala), Arginine (Arg), Asparagine (Asn), Aspartic acid (Asp), Cysteine (Cys), Glutamic acid (Glu), Glutamine (Gln), Glycine (Gly), Histidine (His), Isoleucine (Ile), Leucine (Leu), Lysine (Lys), Methionine (Met), Phenylalanine (Phe), Proline (Pro), Serine (Ser), Threonine (Thr), Tryptophan (Trp), Tyrosine (Tyr) and Valine (Val).

9. The cosmetic composition of claim 1, wherein the PLP is further polymerized or crosslinked.

10. The cosmetic composition of claim 1, wherein the composition is anhydrous.

11. The cosmetic composition of claim 10, wherein the at least one additional cosmetically acceptable ingredient is selected from the group consisting of the structuring agent, the gelling agent which is a hydrophobic gelling agent, the powder, the filler, or a combination of two or more thereof.

12. The cosmetic composition of claim 11, wherein the composition is in the form of the non-compressed powder, the compressed powder or stick, the cosmetic paste, the mascara which is water-proof mascara, the lipstick or the lip gloss.

13. The cosmetic composition of claim 1, wherein the solvent comprises water as major ingredient of the composition, and wherein the at least one additional cosmetically acceptable ingredient comprises the gelling agent which is a hydrophilic gelling agent.

14. The cosmetic composition of claim 1, wherein the composition is in the form of the mascara, wherein the mascara comprises washable mascara, the lipstick, the lip gloss, the lip balm, the cosmetic lotion, the cosmetic cream, or the hair care product, wherein the hair care product comprises a gel, shampoo or a conditioner.

15. The cosmetic composition of claim 1, wherein the composition is multi-phasic and comprises the liquid fatty phase, water as the solvent, or a combination of the liquid fatty phase and water, and the at least one additional cosmetically acceptable ingredient comprises the emulsifier.

16. The cosmetic composition of any of claims 11, 13 and 15, wherein the at least one additional cosmetically acceptable ingredient further comprises a colorant, photoprotective agent, secondary film-former, a cosmetically active agent or a cosmetic adjuvant, wherein the cosmetic adjuvant is selected from the group consisting of emollients, moisturizers, fibers, preservatives, chelators, fragrances, neutralizing agents, and combinations of two or more thereof.

17. The cosmetic composition of claim 1, wherein the solvent comprises water, a water-miscible compound, an ester, oil, a fatty alcohol, or a combination of two or more thereof.

18. A method of making up keratinous tissue, comprising applying to keratinous tissue a cosmetic composition, comprising a) a photoluminescent polymer (PLP) which is a polyester synthesized from a multifunctional monomer containing two carboxylic acid groups and a functional moiety comprising a carboxylic acid group or a hydroxyl group, and a diol, wherein the photoluminescent polymer has grafted thereon or incorporated into the polymer backbone, an amino acid or an amino acid derivative which is S-benzyl-L-cysteine, b) a solvent and c) at least one additional cosmetically acceptable ingredient comprising a structuring agent, a gelling agent, a powder, a filler, an emulsifier, a liquid fatty phase or a combination of two or more thereof, wherein the composition is selected from the group consisting of a non-compressed foundation powder or stick, a compressed foundation powder or stick, a cosmetic paste, mascara, lipstick, lip gloss, lip balm, a cosmetic lotion, a cosmetic cream, and a hair care product.

19. A method of preparing a cosmetic composition for making up keratinous tissue, comprising formulating a) a photoluminescent polymer (PLP) which is a polyester synthesized from a multifunctional monomer containing two carboxylic acid groups and a functional moiety comprising a carboxylic acid group or a hydroxyl group, and a diol, wherein the photoluminescent polymer has grafted thereon or incorporated into the polymer backbone, an amino acid or an amino acid derivative which is S-benzyl-L-cysteine, b) a solvent and c) at least one additional cosmetically acceptable ingredient comprising a structuring agent, a gelling agent, a powder, a filler, an emulsifier, a liquid fatty phase or a combination of two or more thereof, wherein the composition is selected from the group consisting of a non-compressed foundation powder or stick, a compressed foundation powder or stick, a cosmetic paste, mascara, lipstick, lip gloss, lip balm, a cosmetic lotion, a cosmetic cream, and a hair care product.

20. The composition of claim 1, which is a hair care product selected from the group consisting of pre-treatments and post-treatments for color protection, conditioners, leave-in hair treatments, rinse-off hair treatments, styling compositions, combination shampoo/styling compositions and hair volumizing compositions.

21. The composition of claim 20, wherein the styling composition is in the form of a gel, cream, lotion, mousse, spray or wax.

22. The composition of claim 1, wherein the structuring agent is selected from the group consisting of polyorganosiloxane-containing polymers, non-silicone-polyamide copolymers, waxes, and mixtures thereof.

23. The composition of claim 1, wherein the powders and fillers are selected from the group consisting of polyamide particles, nylon fibres, polyethylene powders, microspheres based on acrylic copolymers, melamine-formaldehyde resin particles, urea-formaldehyde resin particles, poly(tetrafluoroethylene) particles, ethylene-acrylate copolymer powders, expanded powders, starch powders, and silicone resin microbeads.

24. The composition of claim 21, wherein the styling composition is in the form of a gel.

25. The composition of claim 1, which is in the form of a non-compressed foundation powder or stick.

26. The composition of claim 1, which is in the form of a compressed foundation powder or stick.

27. The composition of claim 1, which is a cosmetic paste.

28. The composition of claim 1, which is mascara.

29. The composition of claim 1, which is a lipstick.

30. The composition of claim 1, which is a lip gloss.

31. The composition of claim 1, which is a lip balm.

32. The composition of claim 1, which is a cosmetic lotion.

33. The composition of claim 1, which is a cosmetic cream.

34. The method of claim 18, wherein the keratinous tissue is hair and the composition is a hair care product.

35. The method of claim 34, wherein the hair care product is selected from the group consisting of pre-treatments and post-treatments for color protection, conditioners, leave-in hair treatments, rinse-off hair treatments, styling compositions, combination shampoo/styling compositions and hair volumizing compositions.

36. The method of claim 35, wherein the styling composition is in the form of a gel, cream, lotion, mousse, spray or wax.

37. The method of claim 36, wherein the composition is in the form of a gel.

* * * * *